United States Patent [19]

Whittaker

[11] 4,429,132

[45] Jan. 31, 1984

[54] PRODUCTION OF 3-TRICHLOROMETHYL- AND 3-TRIFLUOROMETHYL-PYRIDINES

[75] Inventor: Graham Whittaker, Frodsham, England

[73] Assignee: Imperial Chemical Industries PLC, London, England

[21] Appl. No.: 372,372

[22] Filed: Apr. 27, 1982

[30] Foreign Application Priority Data

May 13, 1981 [GB] United Kingdom ................ 8114624
Jul. 7, 1981 [GB] United Kingdom ................ 8120992
Sep. 3, 1981 [GB] United Kingdom ................ 8126746

[51] Int. Cl.$^3$ .................. C07D 213/61; C07D 213/26
[52] U.S. Cl. .................................... 546/346; 546/345
[58] Field of Search ............................... 546/345, 346

[56] References Cited

U.S. PATENT DOCUMENTS

| 4,205,175 | 5/1980 | Bowden | 546/345 |
| 4,257,857 | 3/1981 | Whittaker et al. | 546/345 |
| 4,284,783 | 8/1981 | Whittaker et al. | 546/345 |
| 4,288,599 | 9/1981 | Nishiyama et al. | 546/345 |
| 4,288,600 | 9/1981 | Roberts et al. | 546/345 |
| 4,291,213 | 12/1980 | Nishiyama et al. | 546/345 |

FOREIGN PATENT DOCUMENTS 2045761A 11/1980 United Kingdom .

Primary Examiner—Henry R. Jiles
Assistant Examiner—Bernard Dentz
Attorney, Agent, or Firm—Cushman, Darby & Cushman

[57] ABSTRACT

3-Trichloromethylpyridines are produced from 3-methylpyridines by reaction with chlorine in the vapor phase in the presence of a metal oxide or metal halide catalyst.

9 Claims, No Drawings

PRODUCTION OF 3-TRICHLOROMETHYL- AND 3-TRIFLUOROMETHYL-PYRIDINES

This invention relates to the production of 3-trichloromethyl- and 3-trifluoromethyl-pyridines.

The compounds 2-chloro-5-trichloromethylpyridine; 2-chloro-5-trifluoromethylpyridine; 2,3-dichloro-5-trichloromethylpyridine and 2,3-dichloro-5-trifluoromethylpyridine are useful intermediates in the preparation of compounds having herbicidal activity, for example compounds described in European Patent Publication No. 0001473.

The compounds 3-trichloromethylpyridine; 3-trifluoromethylpyridine; 3-chloro-5-trichloromethylpyridine and 3-chloro-5-trifluoromethylpyridine are in turn useful in the preparation of certain of the said intermediates via ring-chlorination and/or side-chain fluorination.

Thus, for example, 3-trichloromethylpyridine may be subjected to side-chain fluorination to yield 3-trifluoromethylpyridine, which may be selectively ring-chlorinated to yield 2-chloro-5-trifluoromethylpyridine (as described in European Patent Publication No. 0013474). Similarly, 3-chloro-5-trichloromethylpyridine and 3-chloro-5-trifluoromethylpyridine may be selectively ring-chlorinated to yield respectively 2,3-dichloro-5-trichloromethylpyridine and 2,3-dichloro-5-trifluoromethylpyridine.

We have now found that 3-trichloromethylpyridine may be selectively produced from 3-methylpyridine by a process which may, if desired, readily be integrated with subsequent fluorination to yield 3-trifluoromethylpyridine.

According to the present invention there is provided a process for the production of a 3-trichloromethylpyridine characterised in that a 3-methylpyridine is reacted with chlorine in the vapour phase at a temperature in the range from 200° C. to 350° C. in the presence of a metal oxide or metal halide halogenation catalyst.

The process is especially applicable when the organic starting-material is 3-methylpyridine itself. Further substituents may, however, be present in the pyridine ring; these may be inert substituents (for example chlorine or fluorine atoms) or groups which are themselves subject to chlorination, for example a further methyl group. Thus, for example, 3,5-lutidine may be chlorinated by the process of the present invention to yield 3,5-bis-(trichloromethyl)-pyridine.

The catalyst may be of the type usually regarded as a fluorination catalyst, for example the oxides or fluorides of one or more of chromium, manganese, iron, cobalt and nickel. Alternatively, the metal of the catalyst may be a metal more usually associated with chlorination; thus, for example, the catalyst may comprise a chloride of one or more of the metals just referred to or an oxide, chloride or fluoride of one or more copper, silver, magnesium, calcium, zinc, cadmium and mercury.

The catalyst may be used either in the form of a fixed bed or in the form of a fluidised bed. The metal oxide or halide may be unsupported or may be carried upon a support material, for example aluminium fluoride, alumina, silica or a silica-alumina.

When the catalyst comprises an oxide, fluoride or chloride of copper, and the starting-material is 3-methyl-pyridine itself, a substantial proportion of 3-chloro-5-trichloromethylpyridine may be obtained in the products.

Thus according to another aspect of the present invention there is provided a process for the production of 3-trichloromethylpyridine and/or 3-chloro-5-trichloromethylpyridine which comprises reacting 3-methylpyridine with chlorine at a temperature in the range from 200° C. to 350° C. in the vapour phase in the presence of a catalyst comprising an oxide, chloride or fluoride of copper.

The reaction between 3-methylpyridine and chlorine is preferably carried out at a temperature in the range from 225° C. to 325° C.

The proportion of chlorine is preferably at least 3 moles of chlorine per methyl group of the 3-methylpyridine. The upper limit to the proportion of chlorine depends upon the reaction temperature. At the lower end of the specified temperature range considerably more than 3 moles of chlorine per methyl group of the 3-methylpyridine may be used (for example up to 10 moles of chlorine per methyl group) but at temperatures of 250° C. or above, the use of more than about 5 moles of chlorine per methyl group may lead to products containing 2-chloro-5-trichloromethylpyridine, the proportion of this product increasing as the temperature and/or the proportion of chlorine is increased.

The reaction between the 3-methylpyridine and chlorine is preferably carried out in the presence of an inert diluent, conveniently nitrogen (using, for example, from 2 to 20 moles of nitrogen per mole of the 3-methylpyridine) but other inorganic diluents may be used and organic diluents (for example chlorinated hydrocarbons, especially carbon tetrachloride) may also be used.

The optimum residence time will depend upon the particular catalyst employed, the reaction temperature and the relative proportions of chlorine and 3-methylpyridine; in general suitable residence times are in the range from 1 to 60 seconds.

The 3-trichloromethylpyridine and/or 3-chloro-5-trichloromethylpyridine produced may, if desired, be separated from the other reaction products by conventional methods, for example fractional distillation and/or acid extraction.

Alternatively, the gaseous reaction product may be passed to a second reaction zone wherein the 3-trichloromethylpyridine is reacted with hydrogen fluoride in the vapour phase in the presence of a fluorination catalyst to yield the corresponding 3-trifluoromethylpyridine. Suitable catalysts include the fluorination catalysts already referred to herein. The fluorination is preferably carried out at a temperature in the range from 250° C. to 450° C.

The defined sequence of reaction zones, with separate stages of chlorination and fluorination, enables the overall process to be carried out with high selectivity and good conversion of the 3-methylpyridine into 3-trifluoromethylpyridine and/or 3-chloro-5-trifluoromethylpyridine.

If desired, the 3-trifluoromethylpyridine produced in the second reaction zone may be separated from the reaction products and chlorinated (either in the vapour-phase or in the liquid phase) to yield 2-chloro-5-trifluoromethylpyridine and/or 2,6-dichloro-5-trifluoromethylpyridine as described in our European Application Publication No. 0013474. Similarly, any 3-chloro-5-trifluoromethylpyridine produced may be chlorinated to yield 2,3-dichloro-5-trifluoromethylpyridine using the same general methods. The production of the said further chlorinated derivatives may, however, advantageously be integrated with the production of 3-trifluoromethylpyridine and/or 3-chloro-5-trifluoromethylpyridine by passing the gaseous product from the second reaction zone (as defined hereinbefore) to a third reaction zone wherein 3-trifluoromethylpyridine is reacted with chlorine in the vapour phase to yield 2-chloro-5-trifluoromethylpyridine and/or 2,6-dichloro-5-trifluoromethylpyridine while any 3-chloro-5-trifluoromethylpyridine yields 2,3-dichloro-5-trifluoromethylpyridine.

The invention is illustrated by the following Examples. Unless otherwise stated, all parts and percentages are by weight.

EXAMPLE 1

A stream of vapourised 3-methylpyridine (0.42 mole per hour) was mixed with gaseous chlorine and nitrogen at a temperature of 220° C. to give a reaction mixture containing 4 moles of chlorine and 14 moles of nitrogen per mole of 3-methylpyridine. This mixture was passed down an inconel reactor tube 1 meter in length and 5 cm internal diameter filled with 4 mm pellets of chromia catalyst. (This catalyst had previously been treated with gaseous hydrogen fluoride).

The temperature of the catalyst bed was maintained at 220° C. and the contact time was 8.3 seconds.

The gaseous reaction products were condensed in a water-cooled condenser. (A stream of gaseous hydrogen fluoride was introduced into the stream of the reaction products at a point between the exit from the reactor and the condenser; this hydrogen fluoride served as diluent and as solvent for the chlorinated products; no significant fluorination was detectable).

The condensate was diluted with water, neutralised with aqueous potassium hydroxide solution and then subjected to extraction with chloroform. The chloroform solution was analysed by capillary gas-liquid chromatography, nuclear magnetic resonance and mass spectrometry. The main products were as follows:

| | |
|---|---|
| 3-trichloromethylpyridine | 36% |
| 3-dichloromethylpyridine | 14% |
| 3-monochloromethylpyridine | 12% |
| (unconverted 3-methylpyridine | 10%) |

EXAMPLE 2

The procedure of Example 1 was repeated except that the reaction temperature was 250° C. and the contact time was 7.9 seconds. The main products were:

| | |
|---|---|
| 3-trichloromethylpyridine | 54% |
| 3-dichloromethylpyridine | 15% |
| 3-monochloromethylpyridine | 9% |
| 2-chloro-5-trichloromethylpyridine | 4% |
| 2-chloro-3-dichloromethylpyridine | 2% |

EXAMPLE 3

The procedure of Example 1 was repeated except that the reaction temperature was 310° C. and the contact time was 7.1 seconds. The main products were:

| | |
|---|---|
| 3-trichloromethylpyridine | 48% |
| 3-dichloromethylpyridine | 9% |
| 3-monochloromethylpyridine | 7% |
| 2-chloro-5-trichloromethylpyridine | 10% |
| 2-chloro-3-dichloromethylpyridine | 4% |

EXAMPLE 4

By way of comparison the same general procedure was repeated except that an empty reactor tube was used instead of the bed of catalyst.

The reaction mixture contained 4 moles of chlorine, 8 moles of nitrogen and 5 moles of hydrogen fluoride per mole of 3-methylpyridine. (The hydrogen fluoride was present as diluent and as solvent for the chlorinated products; no significant fluorination was detectable).

The reaction temperature was 360° C. and the contact time was 21 seconds. The main products were:

| | |
|---|---|
| 3-trichloromethylpyridine | 24% |
| 3-dichloromethylpyridine | 20% |
| 2-chloro-3-dichloromethylpyridine | 14% |
| 2-chloro-5-trichloromethylpyridine | 11% |

By comparison with the previous Examples it will be seen that even at the relatively high temperatures and with the longer contact time a lower proportion of 3-trichloromethylpyridine was produced.

EXAMPLE 5

A catalyst was prepared by impregnation of aluminium trifluoride support (mean particle size 150 μm) with aqueous ferric chloride solution to give a catalyst containing 2% Fe by weight of the support.

The catalyst (900 g) was charged to a vertical inconel reactor (50 mm diameter, 1 m long) and fluidised with a stream of nitrogen at 300° C. for 1 hour, followed by treatment with chlorine (2 mol h$^{-1}$) at 300° C. for 30 min.

A stream of 3-methylpyridine (0.42 mole h$^{-1}$) in nitrogen was pre-heated to 220° C. and reacted in the fluidised bed with a stream of chlorine which had similarly been pre-heated to 220° C. The reaction mixture contained 5 moles of chlorine and 10 moles of nitrogen per mole of 3-methylpyridine. The temperature of the fluidised bed was maintained at 310° C.; the residence time in the bed was 6.3 sec.

Analysis of the reaction products by capillary gas chromatography showed the main products to be:

| | |
|---|---|
| 3-trichloromethylpyridine | 53% |
| 3-dichloromethylpyridine | 20% |
| 3-monochloromethylpyridine | 8% |
| 2-chloro-5-trichloromethylpyridine | 7% |

EXAMPLE 6

Aluminium fluoride (1000 g, mean particle size 150 μm) was placed in a vertical reactor (50 mm diameter, 1 m long) and 32 g anhydrous cuprous chloride powder was added. The bed was fluidised with nitrogen and heated to 400° C. After 1 hour the catalyst was treated with chlorine (2 mole h$^{-1}$) for 1 hour.

The catalyst bed was then cooled to 280° C. and 3-picoline (0.42 mole h$^{-1}$) in a stream of nitrogen (pre-heated to 220° C.) was reacted in the bed with chlorine which had similarly been pre-heated to 220° C. The reaction mixture contained 5 moles of chlorine and 10 moles of nitrogen per mole of 3-methylpyridine. The temperature of the bed was maintained at 280° C.; the residence time in the bed was 4.2 sec.

The main products were:

| 3-trichloromethylpyridine | 60% |
| 2-chloro-5-trichloromethylpyridine | 12% |
| 3-chloro-5-trichloromethylpyridine | 10% |
| 2-chloro-3-trichloromethylpyridine | 4% |

The gaseous reaction products leaving the fluidised bed were mixed with gaseous hydrogen fluoride (5 moles HF per mole of 3-methylpyridine initially fed) which had been pre-heated to 300° C. and the mixture thus obtained was passed to a second reactor (25 mm diameter, 1 m long) packed with pellets of the chromia catalyst described in Example 1. The temperature of this catalyst bed was maintained at 330° C.; the residence time was 1.2 sec. The main products from the second reactor were:

| 3-trifluoromethylpyridine | 43% |
| 2-chloro-5-trifluoromethylpyridine | 11% |
| 3-chloro-5-trifluoromethylpyridine | 9% |

EXAMPLE 7

A mixture of 3-methylpyridine, chlorine and nitrogen (containing 5 moles of chlorine and 6 moles of nitrogen per mole of 3-methylpyridine) was fed to a fluidised bed of a chlorination catalyst containing 2% copper prepared by impregnation of aluminium fluoride with cuprous chloride. (Before use the catalyst had been treated with chlorine by passing a stream of gaseous chlorine through the catalyst bed at 400° C. for 4 hours).

The fluidised bed was maintained at 300° C. The residence time of the reaction mixture in the fluidised bed (gas velocity 5 cm sec$^{-1}$) was about 13 seconds.

The gaseous reaction products from the fluidised bed (containing 3-chloro-5-trichloromethylpyridine) were passed, without intermediate separation, to a fixed bed of chromia fluorination catalyst maintained at 330° C. where the reaction products from the fluidised bed were reacted with gaseous hydrogen fluoride (introduced in the proportion of 5 moles HF per mole of 3-methylpyridine present in the feed to the fluidised bed). The residence time in the fixed bed of chromia catalyst was 1 second.

The composition of the products was as follows:

| 3-chloro-5-trifluoromethylpyridine | 15% |
| 2-chloro-5-trifluoromethylpyridine | 28% |
| 2-chloro-3-trifluoromethylpyridine | 9% |
| 3-trifluoromethylpyridine | 24% |

I claim:

1. A process for the production of a 3-trichloromethylpyridine, characterised in that a 3-methylpyridine is reacted with chlorine in the vapour phase at a temperature in the range from 200° C. to 350° C. in the presence of a metal oxide or metal halide halogenation catalyst.

2. A process according to claim 1, characterised in that the catalyst comprises an oxide, fluoride or chloride of one or more of chromium, manganese, iron, cobalt and nickel.

3. A process according to claim 1, characterised in that the catalyst comprises an oxide, fluoride or chloride of one or more of copper, silver, magnesium, calcium, zinc, cadmium, and mercury.

4. A process for the production of 3-trichloromethylpyridine and/or 3-chloro-5-trichloromethylpyridine, characterised in that 3-methylpyridine is reacted with chlorine in the vapour phase at a temperature in the range from 200° C. to 350° C. in the presence of a catalyst comprising an oxide, fluoride or chloride of copper.

5. A process according to claim 1, characterised in that the reaction is carried out at a temperature in the range from 225° C. to 325° C.

6. A process according to claim 1, characterised in that the proportion of chlorine is at least 3 moles per methyl group of the 3-methylpyridine.

7. A process according to claim 1 or claim 4, characterised in that the gaseous reaction product is passed to a second reaction zone wherein the 3-trichloromethylpyridine is reacted with hydrogen fluoride in the vapour phase in the presence of a fluorination catalyst to yield the corresponding 3-trifluoromethylpyridine.

8. A process according to claim 7, characterised in that the gaseous product from the second reaction zone is passed to a third reaction zone wherein 3-trifluoromethylpyridine is reacted with chlorine in the vapour phase to yield 2-chloro-5-trifluoromethylpyridine and/or 2,6-dichloro-5-trifluoromethylpyridine while any 3-chloro-5-trifluoromethylpyridine yields 2,3-dichloro-5-trifluoromethylpyridine.

9. 3-chloro-5-trichloromethylpyridine.

* * * * *